(12) United States Patent
Canuel et al.

(10) Patent No.: US 6,503,234 B1
(45) Date of Patent: Jan. 7, 2003

(54) THIN SANITARY NAPKIN HAVING A FLEXIBILITY SELECTED TO PROVIDE A GOOD COMFORT POTENTIAL WHILE REDUCING BUNCHING

(75) Inventors: Louis Canuel, Repentigny (CA); Christiane Lariviere, Montreal (CA); Roya Mohmad, Montreal (CA); Zulifkar Murji, Verdun (CA); Leonard G. Rosenfeld, East Windsor, NJ (US)

(73) Assignee: Johnson & Johnson Inc. (CA)

( * ) Notice: Subject to any disclaimer, the term of this patent is extended or adjusted under 35 U.S.C. 154(b) by 0 days.

(21) Appl. No.: 09/477,309

(22) Filed: Jan. 4, 2000

Related U.S. Application Data

(63) Continuation-in-part of application No. 09/374,653, filed on Aug. 16, 1999, now abandoned.

(51) Int. Cl.[7] ................................................. A61F 13/20
(52) U.S. Cl. .................................. 604/385.01; 604/378
(58) Field of Search ................................ 604/374, 372, 604/370, 367, 378, 358, 385.01, 385.03, 385.04

(56) References Cited

U.S. PATENT DOCUMENTS

| 5,248,309 A | 9/1993 | Serbiak et al. |
| 5,383,869 A | 1/1995 | Osborn, III |
| 5,866,242 A | * 2/1999 | Tan et al. .................... 428/219 |

FOREIGN PATENT DOCUMENTS

| EP | 0 336 578 A1 | 10/1989 |
| WO | 93/21879 A1 | 11/1993 |
| WO | 98/29076 A1 | 7/1998 |
| WO | 00/41882 A1 | 7/2000 |

* cited by examiner

*Primary Examiner*—Danny Worrell
(74) *Attorney, Agent, or Firm*—James P. Barr

(57) ABSTRACT

A sanitary napkin is disclosed that is thin, highly absorbent and has a flexibility selected to provide good comfort potential and at the same time reduce the likelihood of uncontrolled deformation, known as bunching. In a specific example, the sanitary napkin has a cover layer, an absorbent system and barrier layer. The absorbent system has super-absorbent material in a matrix of cellulosic fibers.

41 Claims, 3 Drawing Sheets

THIN SANITARY NAPKIN HAVING A FLEXIBILITY SELECTED TO PROVIDE A GOOD COMFORT POTENTIAL WHILE REDUCING BUNCHING

This is a continuation-in-part of Ser. No. 09/374,653 filed Aug. 16, 1999 abandoned.

FIELD OF THE INVENTION

The present invention relates to the art of manufacturing structures for absorbing body exudate, more particularly to a sanitary napkin that is thin, absorbent and has a flexibility selected to provide a good comfort potential and at the same time reduce the likelihood of uncontrolled deformation in use.

BACKGROUND OF THE INVENTION

In the past recent years, the sanitary protection industry has developed improved sanitary napkins that are highly absorbent and at the same time they are thin which significantly enhances their comfort potential. The conventional wisdom dictates that the comfort potential of the sanitary napkin is directly related to its flexibility, in particular the flexibility in the lateral direction. Hence, in order to improve the comfort, sanitary napkin designers have almost universally tried to create a product which is as flexible as possible. The idea behind this approach is that the flexible product will create less discomfort to the user particularly when the sanitary napkin is compressed between the thighs of the wearer.

However, sanitary napkins that are highly flexible are known to suffer from high failure rates. This can be traced to the inability of the sanitary napkin to maintain firm contact with the vaginal opening of the user. As a consequence, the menstrual fluid discharged from the vaginal opening cannot be captured immediately into the sanitary napkin and leakage that can stain the user' undergarment may occur. This is somewhat paradoxical since a sanitary napkin that is highly flexible should, at least in theory adapt well to the anatomy of the user and maintain the condition of close contact against the skin even when the user is moving or performing another physical activity.

However, studies have demonstrated that sanitary napkins that are highly flexible when in place in the crotch portion of the user and when compressed by the user's thighs deform laterally according to a random or uncontrolled manner. This results into the so-called "bunching" problem. A sanitary napkin that bunches is compressed in a way to significantly reduce its fluid absorption area and prevent close conformation with the vaginal opening. This may explain the high incidence of failure rates observed in connection with sanitary napkins that are very flexible.

One possible manner to increase the lateral rigidity of a sanitary napkin that is taught by the prior art is to calendar the napkin between a pair of rolls. This operation stiffens the entire product by the effect of compaction. A drawback of this operation, however, is to negatively affect the absorption capacity of the sanitary napkin. The compaction effectively reduces the amount of void volume in the absorptive layers of the sanitary napkin, thus reducing its ability to store liquid.

Thus, there exists in the industry a need to provide a sanitary napkin that is thin, highly absorbent and has good comfort potential and at the same time is capable of reducing the incidence of bunching in use.

SUMMARY OF THE INVENTION

The present invention provides a sanitary napkin that has a thickness less than about 5 mm, a test capacity of more than about 8 g, a total capacity of more than about 14 g and a flexural resistance in the range from about 400 g to about 800 g. This sanitary napkin has excellent absorption characteristics and at the same time reduces the incidence of bunching. These two characteristics contribute to provide a sanitary napkin that reduces the likelihood of failures.

In a specific example, the sanitary napkin according to the invention has a cover layer, an absorbent system underneath the cover layer and a barrier layer underneath the absorbent system. The absorbent system is preferably a two-layer structure and includes a first absorbent layer and a second absorbent layer. The second absorbent layer includes a blend of cellulosic fibres and superabsorbent material. In a very specific embodiment, the second absorbent layer has been air-laid as a bottom layer of pulp, a middle layer of pulp and superabsorbent disposed in amongst the pulp and a top layer containing at least some pulp.

Other aspects and features of the present invention will become apparent to those ordinarily skilled in the art upon review of the following description of specific embodiments of the invention in conjunction with the accompanying drawings.

DETAILED DESCRIPTION

Figure 1:
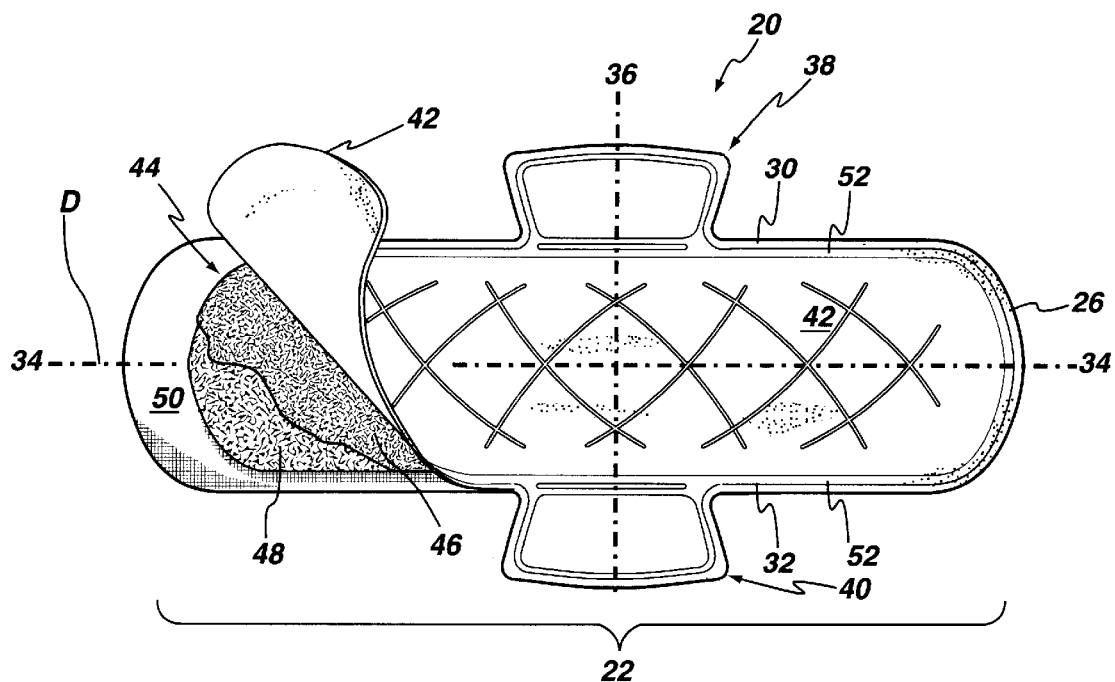
FIG. 1 is a top elevational view of a sanitary napkin in accordance with the present invention, the cover layer of the sanitary napkin being partly removed to show the absorbent system.
Figure 2:
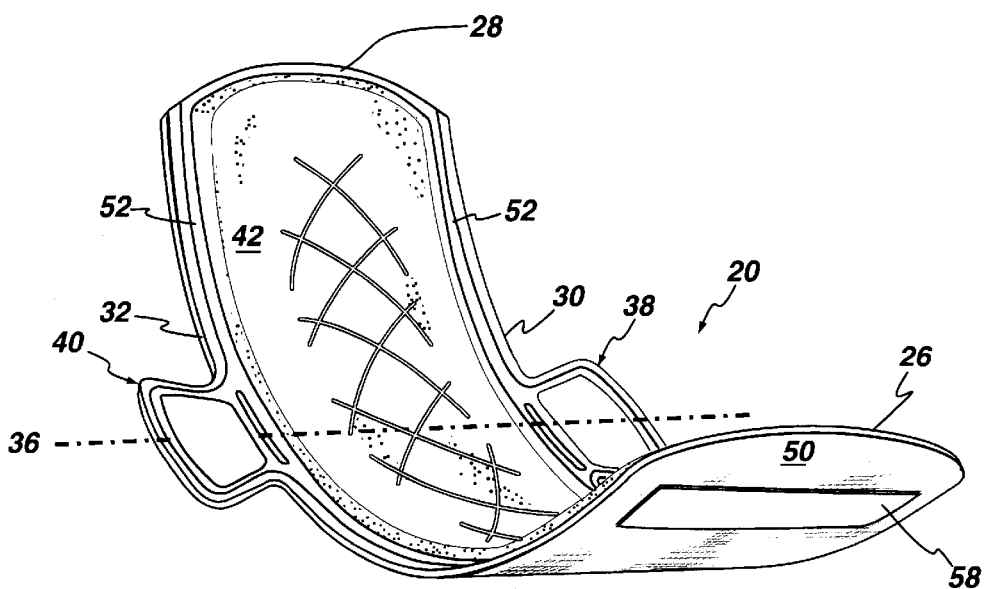
FIG. 2 is a perspective view of the sanitary napkin of FIG. 1, depicted in a position attained when the sanitary napkin is placed in the undergarment of a wearer.

Referring to FIGS. 1 and 2, there is shown an embodiment of the present invention, a feminine sanitary napkin 20.

The sanitary napkin 20 has a main body 22 with a first transverse side 26 defining a front portion thereof and a second transverse side 28 defining a rear portion thereof. Each of these sides is arcuate or of any other suitable shape. The main body also has two longitudinal sides, namely a longitudinal side 30 and a longitudinal side 32. The sanitary napkin 20 has a thickness not exceeding about 5 mm. Preferably, the thickness is less than 3 mm and more preferably is less than 2 mm. In one particular preferred embodiment, the sanitary napkin 20 has a thickness of about 2.8 mm.

The sanitary napkin 20 has a longitudinal centerline 34 that is an imaginary line bisecting the sanitary napkin 20 in two identical halves.

The sanitary napkin 20 shown in the drawings has flaps 38, 40. The flaps 38, 40 project laterally outward from each of the longitudinal sides 30, 32. The flaps 38, 40 are in the shape of an isosceles trapezoid with the top adjoining the longitudinal side and the base at the distal end. This is an example only as other flap shapes can also be used without departing from the spirit of the invention. Furthermore, the present invention is not limited to a sanitary napkin with flaps as the present inventive concept can also be embodied in a sanitary napkin without flaps.

The main body 22 also has an imaginary transverse centerline 36 perpendicular to the longitudinal centerline 34 and simultaneously bisecting the flaps 38, 40.

Figure 4:
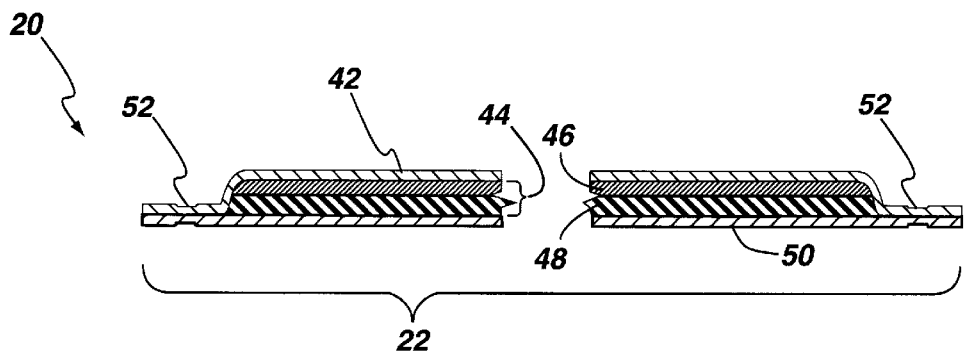
FIG. 4 is a cross-sectional view taken along the longitudinal axis of the sanitary napkin shown in FIG. 3.

As depicted in FIG. 4, the main body 22 is of a laminate construction and preferably comprises a fluid-permeable cover layer 42, an absorbent system 44, and a fluid-impervious barrier layer 50. The absorbent system has preferably two components, namely a first absorbent layer 46 (commonly known as "transfer layer") and a second absorbent layer 48 (commonly known as "absorbent core"). Alternatively, a single layer, namely the second absorbent layer 48, can form the absorbent system 44. Each of these layers is described hereinbelow.

Main Body—Cover Layer

The cover layer 42 may be a relatively low density, bulky, high-loft non-woven web material. The cover layer 42 may be composed of only one type of fiber, such as polyester or polypropylene or it may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. An example is the non-woven cover layer of sanitary napkins sold by Johnson & Johnson Inc. of Montreal, Canada under the trademark Stayfree Ultra-Thin Cottony Dry Cover.

Bi-component fibers may be made up of a polyester core and a polyethylene sheath. The use of appropriate bi-component materials results in a fusible non-woven fabric. Examples of such fusible fabrics are described in U.S. Pat. No. 4,555,446 issued Nov. 50, 1985 to Mays. Using a fusible fabric increases the ease with which the cover layer may be mounted to the adjacent first absorbent layer and/or to the barrier layer.

The cover layer 42 preferably has a relatively high degree of wettability, although the individual fibers comprising the cover may not be particularly hydrophilic. The cover material should also contain a great number of relatively large pores. This is because the cover layer 42 is intended to take-up body fluid rapidly and transport it away from the body and the point of deposition. Advantageously, the fibers which make up the cover layer 42 should not lose their physical properties when they are wetted, in other words they should not collapse or lose their resiliency when subjected to water or body fluid. The cover layer 42 may be treated to allow fluid to pass through it readily. The cover layer 42 also functions to transfer the fluid quickly to the other layers of the absorbent system 44. Thus, the cover layer 42 is advantageously wettable, hydrophilic and porous. When composed of synthetic hydrophobic fibers such as polypropylene or bi-component fibers, the cover layer 42 may be treated with a surfactant to impart the desired degree of wettability.

Alternatively, the cover layer 42 can also be made of polymer film having large pores. Because of such high porosity, the film accomplishes the function of quickly transferring body fluid to the inner layers of the absorbent system. Apertured co-extruded films such as described in U.S. Pat. No. 4,690,679 and available on sanitary napkins sold by Johnson & Johnson Inc. of Montreal, Canada could be useful as cover layers in the present invention.

The cover layer 42 may be embossed to the remainder of the absorbent system 44 in order to aid in promoting fluid transport by fusing the cover to the next layer. Such fusion may be effected locally, at a plurality of sites or over the entire contact surface of cover layer 42 with absorbent system 44. Alternatively, the cover layer 42 may be attached to the absorbent system 44 by other means such as by adhesive.

Main Body—Absorbent System—First Absorbent Layer

Adjacent to the cover layer 42 on its inner side and bonded to the cover layer 42 is a first absorbent layer 46 that forms part of the absorbent system 44. The first absorbent layer 46 provides the means of receiving body fluid from the cover layer 42 and holding it until an underlying second absorbent layer has an opportunity to absorb the fluid.

The first absorbent layer 46 is, preferably, more dense than and has a larger proportion of smaller pores than the cover layer 42. These attributes allow the first absorbent layer 46 to contain body fluid and hold it away from the outer side of the cover layer 42, thereby preventing the fluid from rewetting the cover layer 42 and its surface. However, the first absorbent layer 46 is, preferably, not so dense as to prevent the passage of the fluid through the layer 46 into the underlying second absorbent layer 48. These types of absorbent layers are commonly known as fluid transfer layers or acquisition layers.

The first absorbent layer 46 may be composed of fibrous materials, such as wood pulp, polyester, rayon, flexible foam, or the like, or combinations thereof. The first absorbent layer 46 may also comprise thermoplastic fibers for the purpose of stabilizing the layer and maintaining its structural integrity. The first absorbent layer 46 may be treated with surfactant on one or both sides in order to increase its wettability, although generally the first absorbent layer 46 is relatively hydrophilic and may not require treatment. The first absorbent layer 46 is preferably bonded on both sides to the adjacent layers, i.e. the cover layer 42 and an underlying second absorbent layer 48. An example of a suitable first absorbent layer is a through air bonded pulp sold by BUCK-EYE of Memphis Tennessee under the designation VIZORB 3008.

Main Body—Absorbent System—Second Absorbent Layer

Immediately adjacent to and bonded to the first absorbent layer 46 is the second absorbent layer 48.

In one embodiment, the first absorbent layer 46 has a central width that is at least about the same as the central width of the second absorbent layer 48. In a specific embodiment, this central width is greater than about 64 mm. In another embodiment, the first absorbent layer 46 has a central width that exceeds the central width of the second absorbent layer 48. The term "central width" refers to a specific area of a layer, such as an absorbent layer determinable as follows. A reference point on the sample layer that is disposed beneath the center of the vaginal orifice, when worn, is located. A plane parallel to the transverse centerline 36 and 3.75 centimeters forward from the reference point in the direction of the wearer's mons pubis is located. Another plane parallel to the lateral centerline 36 and 5.0 centimeters rearward from the reference point in the direction of the wearers buttocks is also located. The greatest flat-out, uncompressed, unmanipulated, lateral width of the sample layer between the two planes is the absorbent width of the sample layer.

The central width of the absorbent system, when the absorbent system includes a plurality of absorbent layers is the central width of the layer of the absorbent system that has the largest central width. In a specific example, the central width of the absorbent system exceeds 64 mm.

In one embodiment, the second absorbent layer 48 is a blend or mixture of cellulosic fibers and superabsorbent.

In a specific example, the second absorbent layer 48 is a material containing from about 40 weight percent to about 95 weight percent cellulosic fibers; and from about 5 weight percent to about 60 weight percent SAP (superabsorbent polymers). The material has a water content of less than about 10 weight percent. As used herein, the phrase "weight percent" means weight of substance per weight of final material. By way of example, 10 weight percent SAP means 10 g/m$^2$ SAP per 100 g/m$^2$ basis weight of the material.

Cellulosic fibers that can be used in the second absorbent layer 48 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material.

The second absorbent layer 48 can contain any superabsorbent polymer (SAP), which SAPs are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA60N Type II*, and the product offered by Chemdal International, Inc. of Palatine, Ill., under the designation of 2100A*.

In a specific example the second absorbent layer 48 is a material containing from about 50 to about 95 weight percent cellulosic fibers and, more specifically from about 60 to about 80 weight percent cellulosic fibers. Such a material may contain from about 5 to about 60 weight percent SAP, preferably from about 20 to about 55 weight percent SAP, even more preferably from about 30 to about 45 weight percent SAP, and most preferably about 40 weight percent SAP.

Figure 5:
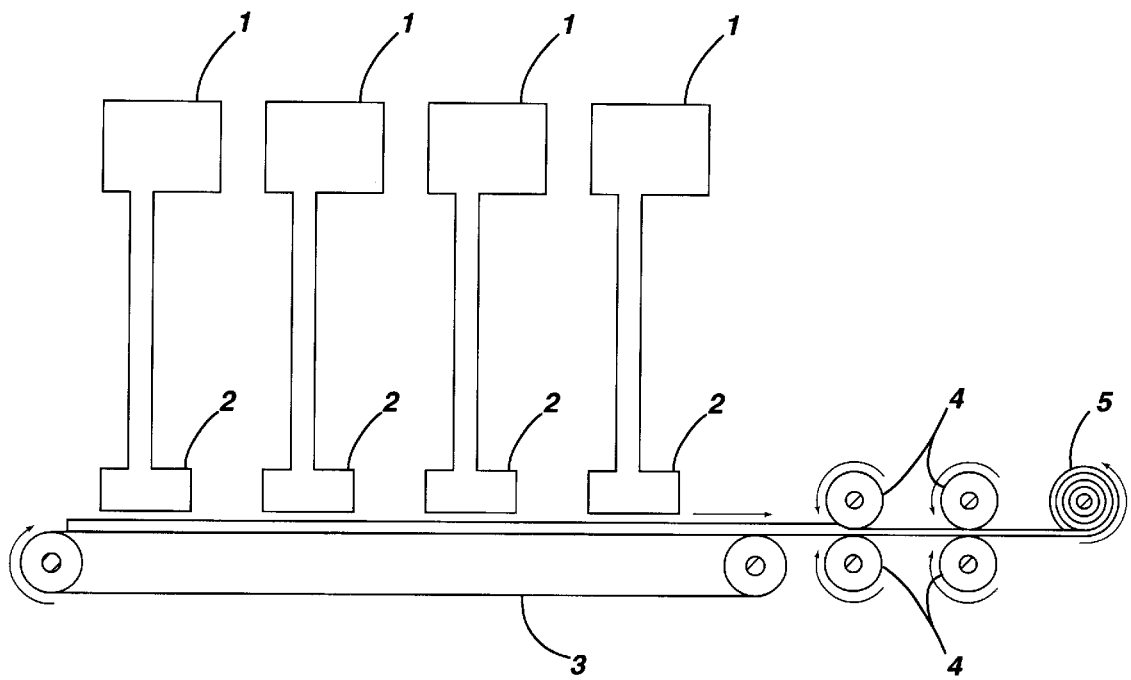
FIG. 5 is a schematic illustration of means for air-laying absorbent material for making an example of an absorbent layer of the sanitary napkin according to the invention, using four air-laying heads followed by means for compacting the air-laid material.

The second absorbent layer 48 can be manufactured by using air-laying means well known in the art (See FIG. 5). In accordance with FIG. 5, cellulosic fibers (e.g., pulp) are processed using a hammer mill to individualize the fibers. The individualized fibers are blended with SAP granules in a blending system 1 and pneumatically conveyed into a series of forming heads 2. The blending and distribution of fibers and SAP granules can be controlled separately for each forming head. Controlled air circulation and winged agitators in each chamber produce uniform mixture and distribution of pulp and SAP. The SAP can be thoroughly and homogeneously blended throughout the material or contained only in specific strata by distributing it to selected forming heads. Fibers (and SAP) from each forming chamber are deposited by vacuum onto a forming wire 3 thus forming a layered absorbent web. The web is subsequently compressed using calenders 4 to achieve desirable density. The densified web is wound into a roll 5 using conventional winding equipment. The forming wire 3 can be covered with tissue paper to reduce the loss of material. The tissue paper layer can be removed prior to calendering or incorporated into the formed material. In a possible variant, the first absorbent layer 46 can be formed integrally with the second absorbent layer 48 to provide a unitized absorbent system 44. This can be achieved by providing the apparatus depicted in FIG. 5 with an additional forming head (not shown in the drawings) to deposit on the second absorbent layer 48, by air laying and prior to calendering, a layer of material to form the first absorbent layer 46.

The second absorbent layer 48 of the present invention is of high density and in a specific example has a density of greater than about 0.25 g/cc. Specifically, the second absorbent layer 48 may have a density in the range of from about 0.30 g/cc to about 0.50 g/cc. More specifically, the density is from about 0.30 g/cc to about 0.45 g/cc and, even more specifically from about 0.35 g/cc to about 0.40 g/cc.

Air-laid absorbents are typically produced with a low density. To achieve higher density levels, such as the examples of the second absorbent layer 48 given above, the air-laid material is compacted using calenders as shown in FIG. 5. Compaction is accomplished using means well known in the art. Typically such compaction is carried out at a temperature of about 100 degrees C. and a load of about 130 Newtons per millimeter. The upper compaction roll is typically made of steel while the lower compaction roll is a flexroll having a hardness of about 85 SH D. It is preferred that both the upper and lower compaction rolls be smooth, although the upper roll can be engraved.

In one embodiment the second absorbent layer 48 has a ratio of Gurley stiffness, measured in milligrams (mg) to density, measured in grams per cubic centimeter (g/cc), of less than about 3700. In a specific example, that ratio of Gurley stiffness to density is less than about 3200 and, more specifically, less than about 3000.

Gurley stiffness is one of many indices of softness. Gurley stiffness measures the bendability or flexibility of absorbent materials. The lower the Gurley stiffness value, the more flexible the material. The Gurley stiffness values are measured using a Gurley Stiffness Tester (Model No. 4171E), manufactured by Gurley Precision Instruments of Troy, N.Y. The instrument measures the externally applied moment required to produce a given deflection of a test strip of specific dimensions fixed at one end and having a concentrated load applied to the other end. The results are obtained in "Gurley Stiffness" values in units of milligrams.

The second absorbent layer 48 is strong in light of its softness. Pad integrity is a well-known measurement of absorbent material strength. In a specific embodiment the second absorbent layer 48 demonstrates strength (high pad integrity) over a wide range of densities. In a specific example the second absorbent layer 48 has a pad integrity, measured in Newtons (N), to density (g/cc) ratio of greater than about 25.0. In a more specific example, that ratio is greater than about 30.0 and, could even be greater than about 35.0. The pad integrity is a test performed on an Instron Universal Testing Machine. Essentially, the test measures the load required to pierce through the test sample, as described in the PFI Method of 1981. A test sample having dimensions of 50 mm by 50 mm is clamped on the Instron with a suitable fastening device. A 20 mm diameter piston traveling at the rate of 50 mm/min punctures the stationary sample. The force required to puncture the sample is measured in Newtons (N).

The second absorbent layer 48 can be prepared over a wide range of basis weights. The second absorbent layer 48 can have a basis weight in the range of from about 100 g/m² to about 700 g/m². In a specific example, the basis weight ranges from about 150 g/m² to about 350 g/m². Preferably the basis weight ranges from about 200 g/m² to about 300 g/m² and, more preferably, to about 250 g/m².

The second absorbent layer 48 can be formed as three or four lamina or strata. Those strata include a bottom layer, one or two middle layers and a top layer. Specific examples of three and four layer material are set forth below. The SAP can be included in any or all of the layers. The concentration (weight percent) of SAP in each layer can vary as can the nature of the particular SAP.

An interesting characteristic of the second absorbent layer 48 is its ability to retain SAP when subjected to mechanical stress. The second absorbent layer 48 retained over 85 percent by weight of its SAP content when subjected to 10 minutes of rigorous shaking. Specifically, a material of this invention retains over 90 percent, more specifically over 95 percent and, even more specifically over 99 percent of its SAP under these mechanical stresses. The percent of SAP retained was determined by shaking the material in a Ro-Tap Sieve Shaker manufactured by W. S. Tyler Co., Cleveland Ohio. More specifically the sample is placed in a 28-mesh (Tyler series) sieve. Additional sieves of 35-mesh and 150-mesh were attached to the first sieve forming a column of increasingly fine sieves. The column of sieves was capped on either end to prevent the loss of fiber and/or SAP. The sieve column was placed in the shaker and agitated for 10 minutes. The amount of SAP granules shaken loose from the sample, "free SAP", was determined by combining the residue contained in each of the sieves and separating the cellulosic fiber from the SAP.

Even where prepared as from multiple layers, the final thickness of the formed second absorbent layer 48 is low. The thickness can vary from about 0.5 mm to about 2.5 mm. In a specific example, the thickness is from about 1.0 mm to about 2.0 mm and, even more specifically from about 1.25 mm to about 1.75 mm.

One embodiment of the second absorbent layer 48 particularly well suited for use in the sanitary napkin 20 is depicted in FIG. 6. Such second absorbent layer 48 has a basis weight of from about 200 g/m² to about 350 g/m² and a density between about 0.3 g/cc and 0.5 g/cc. In a specific example, the density is from about 0.3 g/cc to about 0.45 g/cc and, more specifically about 0.3 g/cc to about 0.4 g/cc.

Figure 6A:
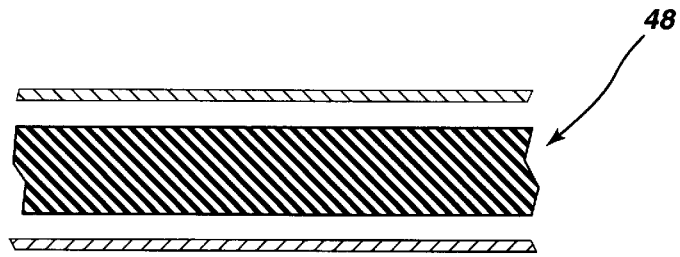
FIGS. 6($a$) and 6($b$) show three and four stratum embodiments, respectively, of the absorbent layer that can be used in the sanitary napkin in accordance with the invention.

The second absorbent layer 48 depicted in FIG. 6(a) is air-laid as three strata: a bottom layer of pulp (without superabsorbent) with a basis weight of about 25 g/m²; a middle layer with a basis weight of about 150 g/m² and which contains from about 10 to about 30 g/m² superabsorbent and from about 120 g/m² to about 140 g/m² pulp; and a top layer of pulp (without superabsorbent) with a basis weight of about 25 g/m². Relative to the total basis weight of the second absorbent layer 48, the level of superabsorbent ranges from about 5 to about 15 weight percent (g/m² of superabsorbent per g/m² material). In a specific example, the level of superabsorbent is from about 7.5 weight percent to about 12.5 weight percent of the material. More specifically, the material contains about 10 weight percent of superabsorbent. Thus, the middle layer of the material could contain from about 15 g/m² to about 25 g/m² superabsorbent and from about 125 g/m² to about 135 g/m² pulp and, more specifically about 20 g/m² superabsorbent and about 130 g/m² pulp. The middle layer containing pulp and superabsorbent can be laid down as a homogeneous blend or as a heterogeneous blend wherein the level of superabsorbent varies with proximity to the bottom layer.

Figure 6B:
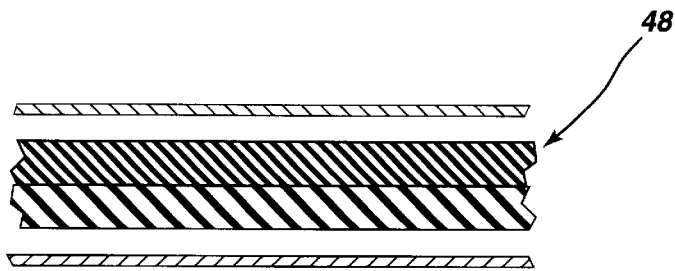

In another embodiment depicted in FIG. 6(b), the second absorbent layer 48 is air-laid as four strata. In this embodiment, the middle layer referred to above is replaced with two middle layers: a first middle layer adjacent the top layer and a second middle layer adjacent the bottom layer. Each of the first and second middle layers independently comprises from about 10 to about 30 g/m² superabsorbent and from about 40 g/m² to about 65 g/m² pulp. When it is desired to keep absorbed fluid away from the cover layer 42 the amount of superabsorbent in the first and second middle layers is adjusted such that there is a higher level of superabsorbent in the second middle layer. The superabsorbent in the first and second middle layers can be the same or a different superabsorbent.

In one embodiment, the cellulosic fiber for use in the second absorbent layer 48 is wood pulp. There are certain characteristics of wood pulp that make it particularly suitable for use. Cellulose in most wood pulps has a crystalline form known as Cellulose I which can be converted to a form known as Cellulose II. In the second absorbent layer 48, wood pulp with a substantial portion of the cellulose as Cellulose II could be used. Similarly, pulps having an increased fiber curl value are advantageous. Finally, pulps having reduced levels of hemicellulose are preferred. Means for treating pulps so as to optimize these characteristics are well known in the art. By way of example, treating wood pulp with liquid ammonia is known to convert cellulose to the Cellulose II structure and to increase the fiber curl value. Flash drying is known to increase the fiber curl value of pulp. Cold caustic treatment of pulp decreases hemicellulose content, increases fiber curl and converts cellulose to the Cellulose II form. Thus it could be advantageous that the cellulosic fibers used to produce the material of this invention contain at least a portion of cold caustic treated pulp.

A description of the cold caustic extraction process can be found in U.S. patent application Ser. No. 08/370,571, filed on Jan. 18, 1995, pending which application is a continuation-in-part application of U.S. patent application Ser. No. 08/184,377, now abandoned filed on Jan. 21, 1994. The disclosures of both of these applications are incorporated in their entirety herein by reference.

Briefly, a caustic treatment is typically carried out at a temperature less than about 60 degree C., but preferably at a temperature less than 50 degree C., and more preferably at a temperature between about 10 degree C. to 40 degree C. A preferred alkali metal salt solution is a sodium hydroxide solution newly made up or as a solution by-product in a pulp or paper mill operation, e.g., hemicaustic white liquor, oxidized white liquor and the like. Other alkali metal salts such as ammonium hydroxide and potassium hydroxide and the like can be employed. However, from a cost standpoint, the preferable salt is sodium hydroxide. The concentration of alkali metal salts is typically in a range from about 2 to about 25 weight percent of the solution, and preferably from about 6 to about 18 weight percent. Pulps for high rate, fast absorbing applications are preferably treated with alkali metal salt concentrations from about 10 to about 18 weight percent.

For further details on the structure and the method of construction of the second absorbent layer 48 the reader is invited to refer to the U.S. Pat. No. 5,866,242 granted on Feb. 2, 1999 to Tan et al. The contents of this document are hereby incorporated by reference.

Main Body—Barrier Layer

Underlying the absorbent system 44 is a barrier layer 50 comprising liquid-impervious film material so as to prevent liquid that is entrapped in the absorbent system 44 from egressing the sanitary napkin and staining the wearer's undergarment. The barrier layer 50 is made preferably of polymeric film.

The cover layer 42 and the barrier layer 50 are joined along their marginal portions so as to form an enclosure or flange seal that maintains the absorbent system 44 captive. The joint may be made by means of adhesives, heat-bonding, ultrasonic bonding, radio frequency sealing, mechanical crimping, and the like and combinations thereof. The peripheral seal line is shown in FIG. 1 by the reference numeral 52.

Flaps

The flaps 38 and 40 are preferably made as integral extensions of the cover layer 42 and the barrier layer 50. These integral extensions are joined to one another along their marginal seal portions by adhesives, heat-bonding, ultrasonic bonding, radio frequency sealing, mechanical crimping, and the like and combinations thereof. Most preferably, such joining is made at the same time the cover layer 42 and the barrier layer 50 are bonded to one another to enclose the absorbent system 44. Alternatively, the flaps may include absorbent material between the cover layer and the barrier layer extensions. Such absorbent material may be an extension of the first absorbent layer 46, the second absorbent layer 48 or both.

Adhesive System

Figure 3:
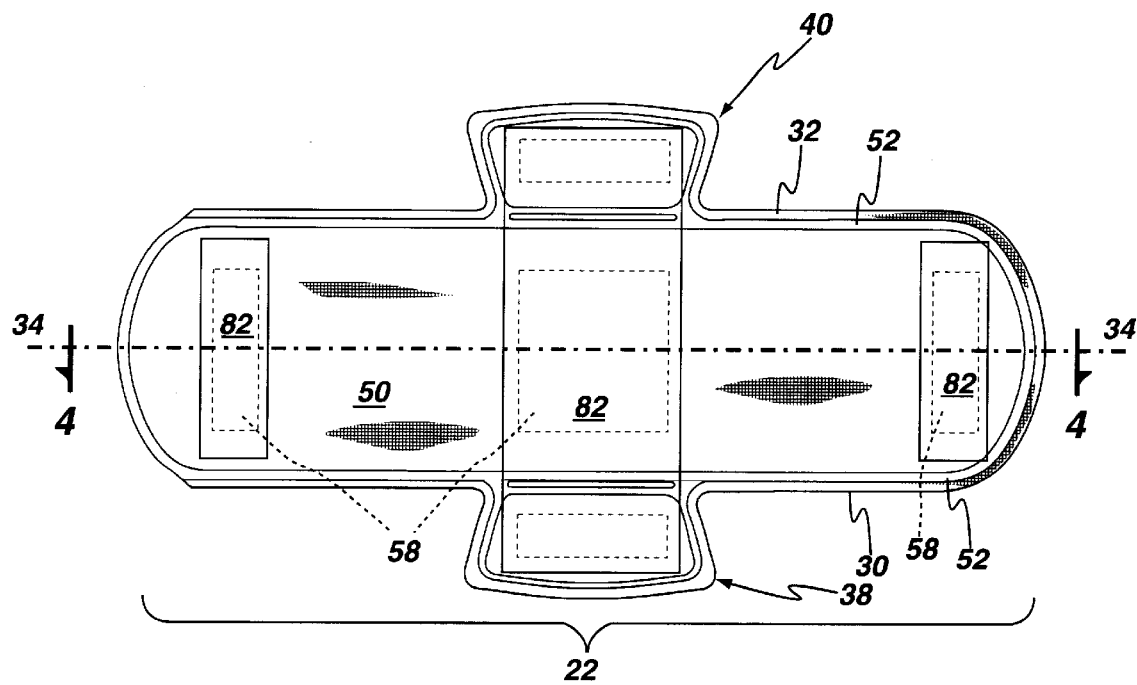
FIG. 3 is a bottom plan view of the sanitary napkin shown in FIG. 1.

Referring to FIGS. 2 and 3, in order to enhance the stability of the sanitary napkin, the garment facing surface of the barrier layer is provided with positioning adhesive material 58, typically hot-melt adhesive material capable of establishing a temporary bond with the undergarment material. A suitable material is the composition designated HL-1491 XZP commercially available from H. B. Fuller Canada, Toronto, Ontario, Canada. The positioning adhesive 58 may be applied to the garment-facing surface of the barrier layer 50 in various patterns, including complete adhesive coverage, parallel longitudinal lines, a line of adhesive following the perimeter of the structure, transverse lines of adhesive or the like.

Standard release paper 82 (shown only in FIG. 3) covers the positioning adhesive 58 before the napkin is used to prevent the unwanted adherence of the napkin to itself or foreign objects. The release paper is of conventional construction (e.g. silicone coated wet-laid Kraft wood pulp) and suitable papers are available from Tekkote Corporation (Leonia, N.J., USA), and bear the designation FRASER 30#/61629.

Method of Manufacture

The above-described embodiment of the sanitary napkin 20 is fabricated in a conventional manner in accordance with conventional techniques. Specifically, a laminate structure, sometimes referred to in the art as a web, is created. This laminate structure comprises an expanse of the materials from which the napkin will be created. I.e. the laminate structure comprises the following layers of material in a top-to-bottom order: an expanse of cover layer material; an expanse of first absorbent layer material; an expanse of second absorbent layer material (manufactured as described above); and finally an expanse of barrier layer. Some of the materials are necessarily not continuous within the laminate structure, and where such is the case, they are positioned precisely, one with respect to another, in the relationship they will occupy in the final products. The cover layer material and the barrier layer material are then bonded together by applying pressure in the appropriate positions, and what will become the peripheral seal is created. (The seal may also be made by means of heat-bonding, ultrasonic bonding, radio frequency sealing, mechanical crimping, and the like and combinations thereof.) The sealed structure is then severed by conventional means (i.e. die-cutting, fluid-jet cutting, or by laser) from the web to create a discrete article.

The positioning adhesive material is then applied to the barrier layer in the appropriate positions, and release paper is applied to cover the positioning adhesive. Alternatively, the positioning adhesive, or the positioning adhesive and the release paper may be applied to the web before the individual articles are severed therefrom.

As indicated earlier, the sanitary napkin 20 has a thickness of about 5 mm or less. The apparatus required to measure the thickness of the sanitary napkin is a footed dial (thickness) gauge with stand, available from Ames, with a 2" diameter foot and a readout accurate to 0.001". A digital type apparatus is preferred. If the sanitary napkin sample is individually folded and wrapped, the sample is unwrapped and carefully flattened by hand. The release paper is removed from the sample and it is repositioned back gently across the positioning adhesive lines so as not to compress the sample, ensuring that the release paper lies flat across the sample. Flaps (if any) are not considered when taking the thickness reading of the sample.

The foot of the gauge is raised and the sample is placed on the anvil such that the foot of the gauge is approximately centered to the sample (or in the location of interest on the sample of interest). When lowering the foot, care is taken to avoid allowing the foot to "drop" or that undue force is not applied. A load of 0.07 p.s.i.g. is applied to the sample and the read out is allowed to stabilize for approximately 5 seconds. The thickness reading is then taken. The thickness of the release paper covering the positioning adhesive is deducted from the total thickness.

The sanitary napkin 20 is characterized by excellent absorption properties and at the same time it has a level of flexural resistance sufficient to reduce the incidence of bunching in use. More particularly, the sanitary napkin 20 has a test capacity of more than about 8 g of fluid and a total capacity of more than about 14 g of fluid. The test and total capacities of a sanitary napkin are determined as follows. Any panty adhesive release paper is removed from the napkin to be tested. To determine test capacity, a 4.75 cm by 14.0 cm portion of the sanitary napkin is cut from the portion of the sanitary napkin which would be centered under the vaginal orifice when the sanitary napkin is worn. Total capacity is determined using the entire napkin minus any release paper. The article is weighed to the nearest 0.1 gram. The article is then submerged in a beaker of sterile saline (obtainable from the Baxter Travenol Company of Deerfield, Ill.), such that the article is totally submerged and is not bent or otherwise twisted or folded. The article is submerged for 10 minutes. The article is removed from the saline and suspended for two minutes in a vertical position to allow the saline to drain out of the article. The article is then placed body-facing surface down onto an absorbent blotter, such as the filter paper #631 available from the Filtration Science Corp., Eaton-Dikeman Division of Mount Holly Springs, Pa. A uniform 17.6 grams per square centimeter load is placed over the article to squeeze excess fluid out. The absorbent blotter is replaced every 30 seconds until the amount of fluid transferred to the absorbent blotter is less than 0.5 grams in a 30 second period. Next, the article is weighed to the nearest 0.1 gram and the dry weight of the article is subtracted. The difference in grams is the test or total capacity of the article, whichever the case may be.

The flexural resistance of the sanitary napkin is preferably in the range from about 400 g to about 800 g. The flexural resistance of a sanitary napkin is measured by peak bending stiffness. Peak bending stiffness is determined by a test that is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexural resistance, simultaneously averaging stiffness in all directions.

The apparatus necessary for the CIRCULAR BEND PROCEDURE is a modified Circular Bend Stiffness Tester, having the following parts:

1. A smooth-polished steel plate platform which is 102.0 mm by 102.0 by 6.35 mm having an 18.75 mm diameter orifice. The lap edge of the orifice should be at a 45 degree angle to a depth of 4.75 mm;
2. A plunger having an overall length of 72.2 mm, a diameter of 6.25 mm, a ball nose having a radius of 2.97 mm and a needle-point extending 0.88 mm therefrom having a 0.33 mm base diameter and a point having a radius of less than 0.5 mm, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice;
3. A force-measurement gauge and more specifically an Instron inverted compression load cell. The load cell has a load range of from about 0.0 to about 2000.0 g;
4. An actuator and more specifically the Instron Model No. 1122 having an inverted compression load cell. The Instron 1122 is made by the Instron Engineering Corporation, Canton, Mass.

In order to perform the procedure for this test, as explained below, five representative sanitary napkins are necessary. From one of the five napkins to be tested, some number "Y" of 37.5 mm by 37.5 mm test specimens are cut. Specimens having portions in which a cover layer is joined directly to a barrier layer or which are a laminate of a cover layer, and a barrier layer without any component of the absorbent system, should not be tested. This test is more concerned with the overall flexibility of the sanitary napkin and not merely the peripheral portions thereof and, therefore, the flexibility of the present invention is more concerned with the flexibility of the absorbent portions of the sanitary napkin.

The test specimens should not be folded or bent by the test person, and the handling of specimens must be kept to a minimum and to the edges to avoid affecting flexural-resistance properties. From the four remaining sanitary napkins, an equal number "Y" of 37.5 mm by 37.5 mm specimens, identical to the specimens cut from the first napkin, are cut. Thus, the test person should have "Y" number of sets of five identical specimens.

The procedure for the CIRCULAR BEND PROCEDURE is as follows. The specimens are conditioned by leaving them in a room that is 21 degree Celsius plus or minus 1 degree Celsius and 50% plus or minus 2.0% relative humidity for a period of two hours. The test plate is leveled. The plunger speed is set at 50.0 cm per minute per full-stroke length. A specimen is centered on the orifice platform below the plunger such that the cover layer 42 of the specimen is facing the plunger and the barrier layer 50 of the specimen is facing the platform. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

Calculations

The peak bending stiffness for each specimen is the maximum force reading for that specimen. Remember that "Y" number of sets of five identical specimens were cut. Each set of five identical specimens is tested and the five values received for that set are averaged. Thus, the test person now has an average value for each of the "Y" sets tested. The flexural resistance for a sanitary napkin is the greatest of these average peak bending stiffnesses.

Applications of the product and methods of the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

I claim:

1. A sanitary napkin adapted to be worn in a crotch portion of an undergarment, said sanitary napkin having a thickness less than about 3 mm, a test capacity of more than about 8 g, a total capacity more than about 14 g and a flexural resistance in the range from about 400 g to about 800 g, said sanitary napkin having an absorbent system, wherein said absorbent system includes superabsorbent material and wherein said absorbent system comprises a first absorbent layer above a second absorbent layer.

2. A sanitary napkin as defined in claim 1, wherein the thickness of the sanitary napkin is less than about 2 mm.

3. A sanitary napkin as defined in claim 1, wherein the thickness of the sanitary napkin is of about 2.8 mm.

4. A sanitary napkin as defined in claim 1, wherein said absorbent system is between a fluid permeable cover layer and a liquid impervious barrier.

5. A sanitary napkin as defined in claim 1, wherein said superabsorbent material is a powder.

6. A sanitary napkin as defined in claim 1, wherein said absorbent system includes a blend of cellulosic fibers and superabsorbent material.

7. A sanitary napkin as defined in claim 6, wherein said second absorbent layer has a basis weight of from about 100 g/m2 to about 700 g/m2 which has been air-laid as a bottom stratum of pulp, a middle stratum of pulp and superabsorbent polymer disposed in amongst the pulp, and a top stratum containing at least some pulp.

8. A sanitary napkin as defined in claim 1, wherein said second absorbent layer has a density of more than about 0.25 g/cc.

9. A sanitary napkin as defined in claim 1, wherein said second absorbent layer includes from about 5 weight percent to about 60 weight percent superabsorbent polymer.

10. A sanitary napkin as defined in claim 1, wherein said second absorbent layer includes from about 20 weight percent to about 55 weight percent superabsorbent polymer.

11. A sanitary napkin as defined in claim 1, wherein said second absorbent layer includes from about 30 weight percent to about 45 weight percent superabsorbent polymer.

12. A sanitary napkin as defined in claim 1, wherein said second absorbent layer includes about 40 weight percent superabsorbent polymer.

13. A sanitary napkin as defined in claim 4, wherein said first absorbent layer comprises a first density and said fluid permeable cover layer comprises a second density, wherein said first density is greater than said second density.

14. A sanitary napkin as defined in claim 7, wherein said first absorbent layer is air laid over the top stratum of pulp of said second layer.

15. A sanitary napkin as defined in claim 7, wherein said sanitary napkin includes a fastener for retaining said sanitary napkin on an undergarment of a wearer.

16. A sanitary napkin as defined in claim 7, wherein said second absorbent layer has a basis weight in the range from about 150 g/m$^2$ to about 350 g/m$^2$.

17. A sanitary napkin as defined in claim 16, wherein said second absorbent layer has a basis weight in the range from about 200 g/m$^2$ to about 300 g/m$^2$.

18. A sanitary napkin as defined in claim 17, wherein said second absorbent layer has a basis weight of about 250 g/m$^2$.

19. A sanitary napkin as defined in claim 16, wherein said second absorbent layer has a density in the range from about 0.3 g/cc to about 0.5 g/cc.

20. A sanitary napkin as defined in claim 19, wherein said second absorbent layer has a density in the range from about 0.3 g/cc to about 0.45 g/cc.

21. A sanitary napkin as defined in claim 7, wherein the middle stratum comprises a first middle stratum adjacent the bottom stratum and a second middle stratum adjacent the top stratum.

22. A sanitary napkin adapted to be worn in a crotch portion of an undergarment having a thickness of less than about 5 mm, a test capacity of more than about 8 g, a total capacity more than about 14 g, a flexural resistance not less than about 400 g, and an absorbent system comprising a first absorbent layer overlying a second absorbent layer, said first absorbent layer having a central width at least as large as a central width of said second absorbent layer wherein said absorbent system includes superabsorbent material.

23. A sanitary napkin as defined in claim 22, wherein said first absorbent layer has a central width exceeding a central width of said second absorbent layer.

24. A sanitary napkin as defined in claim 22, wherein said absorbent system is between a fluid permeable cover layer and a liquid impervious barrier layer.

25. A sanitary napkin as defined in claim 24, wherein said superabsorbent material is a powder.

26. A sanitary napkin as defined in claim 25, wherein said absorbent system includes a blend of cellulosic fibers and superabsorbent material.

27. A sanitary napkin as defined in claim 26, wherein said second absorbent layer has a basis weight of from about 100 g/m2 to about 700 g/m2 which has been air-laid as a bottom stratum of pulp, a middle stratum of pulp and superabsorbent polymer disposed in amongst the pulp, and a top stratum containing at least some pulp.

28. A sanitary napkin as defined in claim 27, wherein said second absorbent layer has a density of more than about 0.25 g/cc.

29. A sanitary napkin as defined in claim 28, wherein said second absorbent layer includes from about 5 weight percent to about 60 weight percent superabsorbent polymer.

30. A sanitary napkin as defined in claim 29, wherein said second absorbent layer includes from about 20 weight percent to about 55 weight percent superabsorbent polymer.

31. A sanitary napkin as defined in claim 30, wherein said second absorbent layer includes from about 30 weight percent to about 45 weight percent superabsorbent polymer.

32. A sanitary napkin as defined in claim 31, wherein said second absorbent layer includes about 40 weight percent superabsorbent polymer.

33. A sanitary napkin as defined in claim 24, wherein said first absorbent layer comprises a first density and said fluid permeable cover comprises a second density, wherein said first density is greater that said second density.

34. A sanitary napkin as defined in claim 27, wherein said first absorbent layer is air laid over the top stratum of pulp of said second layer.

35. A sanitary napkin as defined in claim 27, wherein said sanitary napkin includes a fastener for retaining said sanitary napkin on an undergarment of a wearer.

36. A sanitary napkin as defined in claim 27, wherein said second absorbent layer has a basis weight in the range from about 150 g/m$^2$ to about 350 g/m$^2$.

37. A sanitary napkin as defined in claim 36, wherein said second absorbent layer has a basis weight in the range from about 200 g/m$^2$ to about 300 g/m$^2$.

38. A sanitary napkin as defined in claim 37, wherein said second absorbent layer has a basis weight of about 250 g/m$^2$.

39. A sanitary napkin as defined in claim 22, wherein said second absorbent layer has a density in the range from about 0.3 g/cc to about 0.5 g/cc.

40. A sanitary napkin as defined in claim 39, wherein said second absorbent layer has a density in the range from about 0.3 g/cc to about 0.45 g/cc.

41. A sanitary napkin as defined in claim 27, wherein the middle stratum comprises a first middle stratum adjacent the bottom stratum and a second middle stratum adjacent the top stratum.

* * * * *